United States Patent [19]
Berndt

[11] Patent Number: 5,686,300
[45] Date of Patent: Nov. 11, 1997

[54] FLUORESCENCE DETECTOR

[75] Inventor: Klaus W. Berndt, Stewartstown, Pa.

[73] Assignee: Becton Dickinson and Company, Franklin Lakes, N.J.

[21] Appl. No.: 526,795

[22] Filed: Sep. 11, 1995

[51] Int. Cl.$^6$ .................................................. C12M 1/34
[52] U.S. Cl. ........................... 435/287.5; 435/288.7; 435/808; 422/82.07; 422/82.08; 250/458.1
[58] Field of Search .............................. 435/4, 29, 31, 435/34, 287.1, 287.4, 287.5, 288.1, 288.7; 250/458.1, 459.1, 461.1, 461.2; 422/82.07, 82.08

[56] References Cited

U.S. PATENT DOCUMENTS

| | | | |
|---|---|---|---|
| 5,151,869 | 9/1992 | Alcala | 364/497 |
| 5,202,570 | 4/1993 | Tanaka et al. | 250/575 |
| 5,371,016 | 12/1994 | Berndt | 435/291 |

FOREIGN PATENT DOCUMENTS

| | | | |
|---|---|---|---|
| 567232 | 10/1993 | European Pat. Off. | 435/288.7 |

OTHER PUBLICATIONS

Berndt et al. "Electroluminescent Lamp–Based Phase Fluorometer and Oxygen Sensor." Analytical Biochemistry, vol. 201 (1992), pp. 319–325, 1992.

Brasunas et al., "Infrared detector responsivity measured simultaneously at multiple frequencies." Applied Optics, vol. 29 (1990), pp. 14–15, 1990.

O'Haver et al. "Waveform Effects in Wavelength Modulation Spectrometry," Analytical Chemistry, vol. 49 (1977), pp. 458–461, 1977.

*Primary Examiner*—William H. Beisner
*Attorney, Agent, or Firm*—Alan W. Fiedler

[57] ABSTRACT

A fluorescence detector method and apparatus for detecting biological activities in a fluid specimen, such as blood, urine or sputum, where the specimen and a culture medium are introduced into sealable containers and exposed to conditions enabling a variety of metabolic, physical, and chemical changes to take place in the presence of microorganisms in the sample. In operation, the detector method and apparatus illuminate a chemical sensor material in the sealable container with excitation light which is turned on and off periodically according to a symmetric square wave, split the measured fluorescence photocurrent into two components that represent different harmonics of the symmetric square wave signal, measure the amplitudes of the two components, generate the ratio of the two components, and use that ratio as the sensor output signal to indicate biological activity.

10 Claims, 5 Drawing Sheets

FLUORESCENCE DETECTOR

BACKGROUND OF THE INVENTION

The present invention relates to a wide variety of chemical sensors that are based on changes in fluorescence lifetime. As an example, the present invention is applied to non-invasive apparatus and method for detecting biological activities in a fluid specimen, such as blood, urine or sputum, where the specimen and a culture medium are introduced into sealable containers and exposed to conditions enabling a variety of metabolic, physical, and chemical changes to take place in the presence of microorganisms in the sample. The biological activity being detected by a chemical sensor based on changes in fluorescence lifetime.

Usually, the presence of microorganisms such as bacteria or mycobacteria in a patient's body fluid, particularly blood, is determined using culture vials. A small quantity of body fluid is injected through a sealing robber septum into a sterile vial containing a culture medium. The vial is incubated at a temperature conducive to bacterial growth, e.g., 37° C., and monitored for bacterial growth.

Known instrumental methods detect changes in the $CO_2$ content in culture bottles, which is a metabolic by-product of the bacterial growth. Recently, automated blood culture systems have been developed which use chemical sensors disposed inside a vial. Such sensors often respond to changes in the $CO_2$ concentration by changing their color or by changing their fluorescence intensity (see, e.g., U.S. Pat. No. 4,945,060). The outputs from these sensors are based upon light intensity measurements. This means that errors may occur, particularly if the light sources used to excite the sensors, or the photodetectors used to monitor intensities, exhibit aging effects over time.

In known automated non-invasive blood culture systems, individual light sources, individual spectral excitation and emission filters, and individual photodetectors are arranged adjacent to each vial. Such arrangements result in certain station sensitivity variations from one vial to the next. Due to the fact that most known blood culture sensors generate only a moderate contrast ratio in the measured photocurrent during bacterial growth, extensive and time-consuming calibration procedures and sophisticated detection algorithms are required to operate these systems. Moreover, light sources, spectral filters, and photodetectors with extreme narrow specification tolerances must be utilized. It is also possible to use so-called source monitor photodiodes at each light source, but each of these measures result in increased cost. However, even if it would be possible to equalize all vial stations, certain lot-to-lot variations in the sensor composition and certain vial-to-vial geometry variations would remain.

The disadvantage of such intensity-based sensor arrangements can be overcome by utilizing fluorescent sensors that change their fluorescence lifetime, wherein intensity measurement is replaced with time parameter measurement and intensity changes have no impact on the sensor output signal. Many chemical sensor materials are known that change their fluorescence lifetime with changing oxygen concentration, pH, carbon dioxide concentration, or other chemical parameters (see, e.g., G.B. Patent No. 2,132,348).

A change in sensor fluorescence lifetime is commonly monitored by applying a well-known phase shift method (see, e.g., U.S. Pat. No. 5,030,420), wherein the excitation light is sinusoidally intensity-modulated. That method remits in a sinusoidally intensity-modulated fluorescence emission that is phase-shifted relative to the excitation phase. Phase shift angle, $\theta$, is dependent on the fluorescence lifetime, $\tau$, according to the equation:

$$\tan \theta = \omega\tau \quad (1)$$

where $\omega=2\pi f$, is the circular light modulation frequency.

From equation (1), the disadvantage of the phase shift method becomes evident. If the product $\omega\tau$ is small, then the resulting phase shift $\theta$ is also small. This limits the resolution of the chemical sensor arrangement with regard to the analyte that has to be measured. To overcome this resolution problem, one could increase the modulation frequency. Doing so results in another limitation, the resulting phase shift angles are compressed because they are approaching the 70–90 degree range. The maximum possible phase shift angle for a single exponentially decaying fluorophore is 90 degrees, even for an infinitely long fluorescence lifetime. Due to these limitations, the dynamic range of a chemical sensor based on the phase shift method is limited.

A second disadvantage of the phase shift method is related to the fact that the electronic circuitry introduces an additional phase shift, which depends on the light modulation frequency. It is therefore common practice to use a non-fluorescent scattering medium in order to determine the electronic phase shift, and to subtract this value from the one which is observed while monitoring fluorescence. Unfortunately, the electronic phase shift can change over time. Therefore, the scatter measurement has to be repeated, or the system switches periodically between fluorescence and scatter measurement. This, however, results in a higher complexity of the sensor arrangement.

Another disadvantage of the phase shift method is caused by the fact that the phase of the excitation light may show a drift relative to the phase of the modulation driving signal. This artifact is known for internally modulated lasers, and also for light-emitting diodes, acousto-optic modulators and for electrooptic modulators. The consequence is that the phase information for the excitation modulation can not be derived from the electronic driving signal, but has to be measured via an auxiliary photodetector. Again, this represents an increase in the complexity of the sensor arrangement.

Still another disadvantage of the phase shift method results, if fluorophores are utilized that react via lifetime quenching. In this case, the relationship between the measured phase shift and the analyte concentration is a non-linear one. In other words, the sensor resolution for a low analyte concentration is high, but it decreases with increasing analyte concentration. This limits the dynamic range of the sensor, and is not acceptable for many practical applications.

It would also be possible to monitor the fluorescence lifetime by measuring the modulation degree of the fluorescence which is emitted by the fluorophore. In this case, the excitation light is, as in the phase shift method, modulated sinusoidally. This results in a sinusoidally modulated fluorescence emission, where the modulation degree, $m_F$, depends on the lifetime according to the equation $$m_F = \frac{m_{EX}}{\sqrt{1+(\omega\tau)^2}} \quad (2)$$

In equation (2), $m_{EX}$ is the modulation degree of the excitation light source.

The modulation degree, $m$, of a sinusoidally modulated signal is defined as $$m = \frac{AC}{DC} \quad (3)$$

where AC means haft of the peak-to-peak amplitude of the time-varying component, and DC means the component obtained by averaging over at least one sinusoidal period. In practice, the two components are separated by splitting the photodetector signal into two channels. One channel comprises a high pass filter and measures the AC component. The other channel comprises a low pass filter and measures only the DC component. A ratio device is employed to generate a sensor output signal AC/DC=m.

Such a modulation method has not found practical application in fluorescence sensor apparatus, since any change in the photodetector dark current or any daylight leaking into the sensing apparatus, would cause a change in the measured DC component. This, of course, would generate an error in the sensor output signal. It has been proposed already to overcome this problem by turning the excitation light source periodically on and off, and subtracting the signal $DC_{dark}$, which is measured while the source is off, from the signal DC, which is measured while the source is on, to calculate a corrected signal $DC_{corr}$ which is then used to calculate the true modulation degree. This correction procedure requires additional electronic modules such as a lock-in amplifier, and results in an increased complexity of the apparatus.

A second disadvantage of a possible modulation method is the fact that equation (2) is highly non-linear. Optimum sensor resolution is only obtained in a relatively narrow range for the so-called frequency lifetime product, ωτ. It has already been proposed to overcome this limitation by automatically tuning ω in such a way that the frequency lifetime product ωτ is kept constant while τ is changing. This, however, would also result in a significant increase in complexity. Therefore, a need exists to overcome the disadvantages of the known sensing methods.

SUMMARY OF THE INVENTION

It is an objective of the present invention to overcome the above problems of the prior art by providing an arrangement and the operational principle for a fluorescence detector that is based on changes in fluorescence lifetime, where a high dynamic range with regard to the analyte is achieved, where the sensor resolution is almost independent of the analyte concentration, where changes in the photodetector dark current or changes in the intensity of light leaking into the apparatus have no impact on the sensor output signal, and which is simple in construction so that it can be produced at low cost.

According to the present invention, the above objective is achieved by an apparatus and method for illuminating a chemical sensor material with excitation light which is turned on and off periodically according to a symmetric square wave, splitting the measured fluorescence photocurrent into two AC components that represent different harmonics of the square-wave signal, measuring the amplitudes of the two components, generating the ratio of the two components, and using this ratio as the sensor output signal.

By using chemical sensors that are based on changes in fluorescence lifetime, production-related lot-to-lot variations in the sensor composition, small changes in the sensor position, changes in the light source intensity, changes in optical filter characteristics, and sensitivity changes in the photodetector have no impact on the sensor output signal. Therefore, the present invention allows for simplified sensing algorithms and for an excellent long-time stability of the instrument. Finally, the number of optical and electronic parts that are required to operate the sensor is reduced to a minimum, which has a cost reduction effect compared to known sensor apparatus based on fluorescence lifetime.

These and other features, objects, benefits and advantages of the present invention will become more apparent upon reading the following detailed description of the preferred embodiments, along with the appended claims in conjunction with the drawings, wherein reference numerals identify corresponding components.

DETAILED DESCRIPTION

Figure 1:
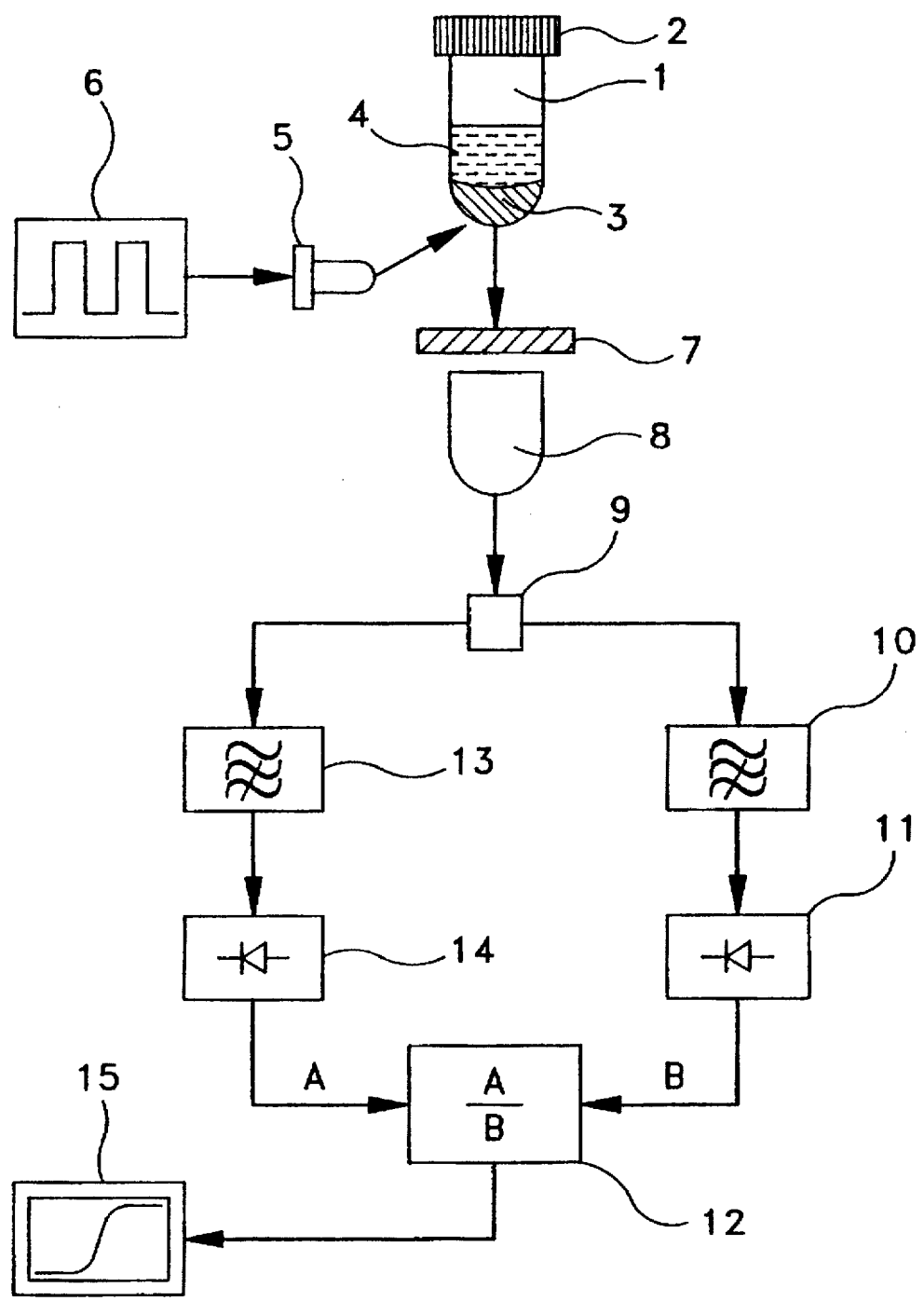
FIG. 1 shows a fluorescence detector arrangement according to the present invention.

A fluorescence detector arrangement embodying the principles and concepts of the present invention is depicted schematically in FIG. 1. In this arrangement, the specimen and a culture medium 4 are introduced into an optically transparent container 1 that is sealed up by a cap 2. A fluorescent chemical sensor material 3 is disposed to the inner wall or to the inner bottom of container 1, and is illuminated by an excitation light source 5, preferably by a blue or green light-emitting diode ("LED"). Light source 5 is connected to an electronic signal source 6 that provides a symmetric square-wave signal that is switching between the states off ("ZERO") and on ("HIGH").

Fluorescence light reemerging from sensor material 3 is detected by means of a photodetector 8 such as a photomultiplier. An emission filter 7 is arranged between sensor material 3 and photodetector 8 in order to reject backscattered excitation light. The signal output of photodetector 8 is fed to a power splitter 9. One output of power splitter 9 is connected to the input of a first band pass filter 10. The output of filter 10 is connected via a first high-frequency voltmeter 11 to the B-input of an A/B ratio unit 12. The first band pass filter 10 is tuned to one harmonic of the square-wave frequency sent by signal source 6. The other output of power splitter 9 is connected to the input of a second band pass falter 13. The output of filter 13 is connected via a second high-frequency voltmeter 14 with the A-input of the A/B ratio unit 12. The second band pass falter 13 is tuned to another harmonic of the square-wave frequency sent by signal source 6. Finally, the output channel of ratio unit 12 is connected to a signal recorder 15.

In operation, light source 5 illuminates chemical sensor material 3 with square-wave modulated excitation light having a time-dependent excitation light intensity, E(t), in the form $$E(t) = \frac{2a}{\pi} \left[ \frac{c}{2} + \sum_{k=1}^{\infty} \frac{\sin(kc)}{k} \cos(k\omega t) \right] \quad (4)$$

where t is time, a is the square-wave amplitude, c is describing the duty cycle, and ω is the square-wave frequency. If we use a symmetrical square wave, c=π/2, all even harmonics are equal to zero and equation (4) reads $$E(t) = a \left[ \frac{1}{2} + \frac{2}{\pi} \cos(\omega t) - \frac{2}{3\pi} \cos(3\omega t) + \frac{2}{5\pi} \cos(5\omega t) - \ldots \right] \quad (5)$$

The re-emitted fluorescence intensity, F(t), has a rather complex course in the time domain. However, by tuning the first and the second band pass filters to different harmonics of the square-wave signal, two AC photocurrent components are generated that are sinusoidally modulated and do not contain a DC bias. If the first band pass filter is tuned to the first harmonic, and the second band pass filter is tuned to the third harmonic, the output signal, R, of ratio unit 12 is given by the following equation (6)

$$R(\omega, \tau) = \frac{1}{3} \sqrt{\frac{1 + (\omega\tau)^2}{1 + (3\omega\tau)^2}} \quad (6)$$

As an example, we assume a fluorophore with a lifetime, τ, that depends on the concentration of oxygen, O, according to the Stern-Volmer law $$\tau(O) = \frac{\tau_o}{1 + qO} \quad (7)$$

where q is a quenching constant.

Figure 2:
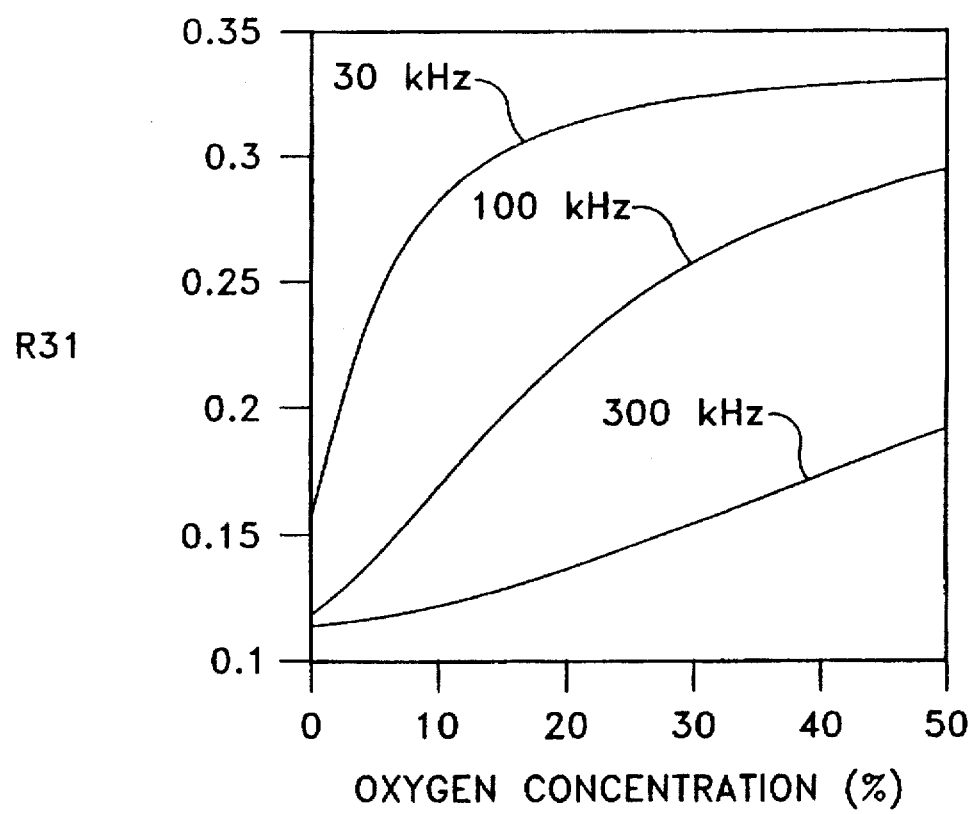
FIG. 2 is a plot showing the ratio of the third and the first harmonic versus oxygen concentration for a fluorophore that is illuminated with a square-wave modulated light intensity and quenched according to a Stern-Volmer relationship.

FIG. 2 depicts the ratio R31 of the third and the first harmonic versus oxygen concentration for a fluorophore with τo=4.74 μs and with q=0.29/%, the fluorophore being illuminated with a square-wave modulated light intensity and quenched according to the Stern-Volmer relationship. The three curves correspond to square-wave frequencies of 30, 100, and 300 kHz, respectively. As can be seen from this figure, an almost linear relationship between R31 and O can be established by selecting an optimum ω.

Figure 3:
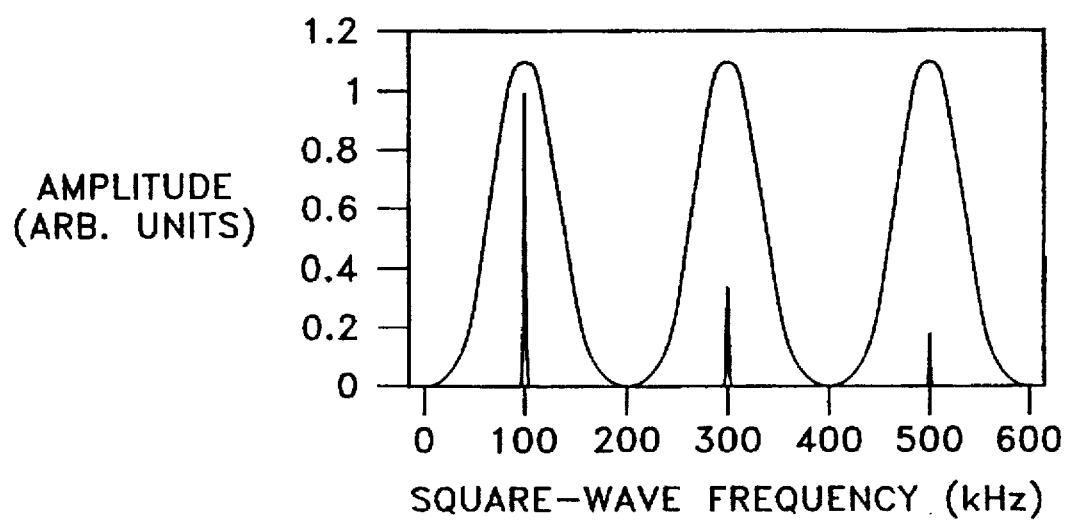
FIG. 3 is a plot showing the relative amplitudes of the first, third and fifth harmonic for a 100-kHz square wave and possible band pass filter transmission curves.

FIG. 3 illustrates the relative amplitudes of the first, third and fifth harmonics for a 100 kHz symmetrical square wave signal. The figure shows that even the fifth harmonic has a sufficiently high amplitude. The figure also shows that the band pass filters are not required to have a high Q value, because the second and forth harmonics are missing.

Figure 4:
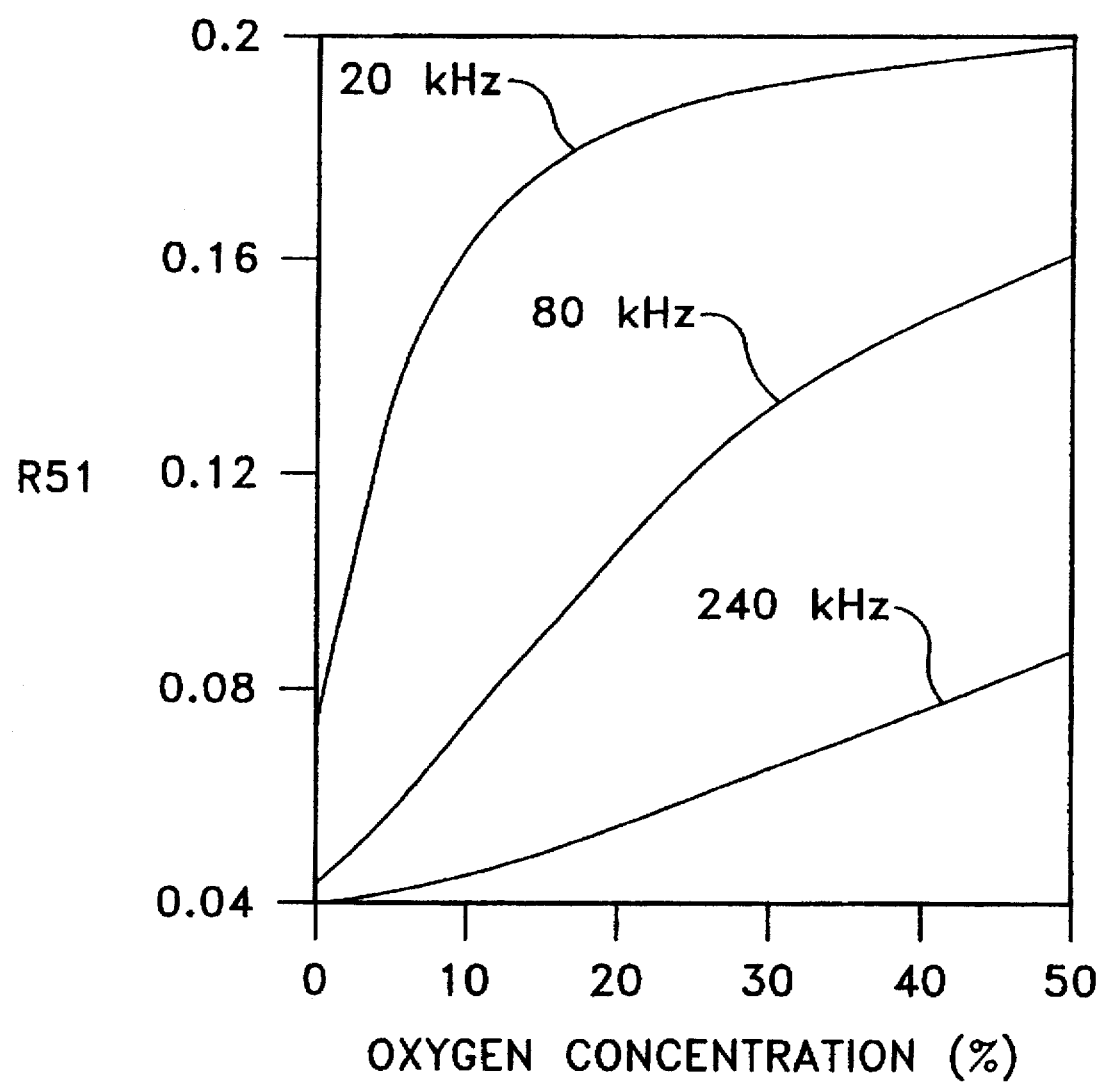
FIG. 4 is a plot showing the ratio of the fifth and the first harmonic versus oxygen concentration.

FIG. 4 depicts the ratio R51 of the fifth and the fh'st harmonic versus oxygen concentration for the same fluorophore as in FIG. 2. The three curves correspond to square-wave frequencies of 20, 80 and 240 kHz, respectively. As in FIG. 2, an almost linear relationship between R51 and O can be established by selecting an optimum ω. Using the fifth and the first harmonic results in a higher contrast between low and high oxygen concentration.

As has been mentioned already, most known blood culture systems detect changes in the carbon dioxide content of the culture bottles, which is a metabolic by-product of the bacterial growth. For historical reasons, growth curves are preferred that show a signal which increases over time. Also, many sophisticated detection algorithms have been developed that are oriented towards positive-going growth curves.

Figure 5:
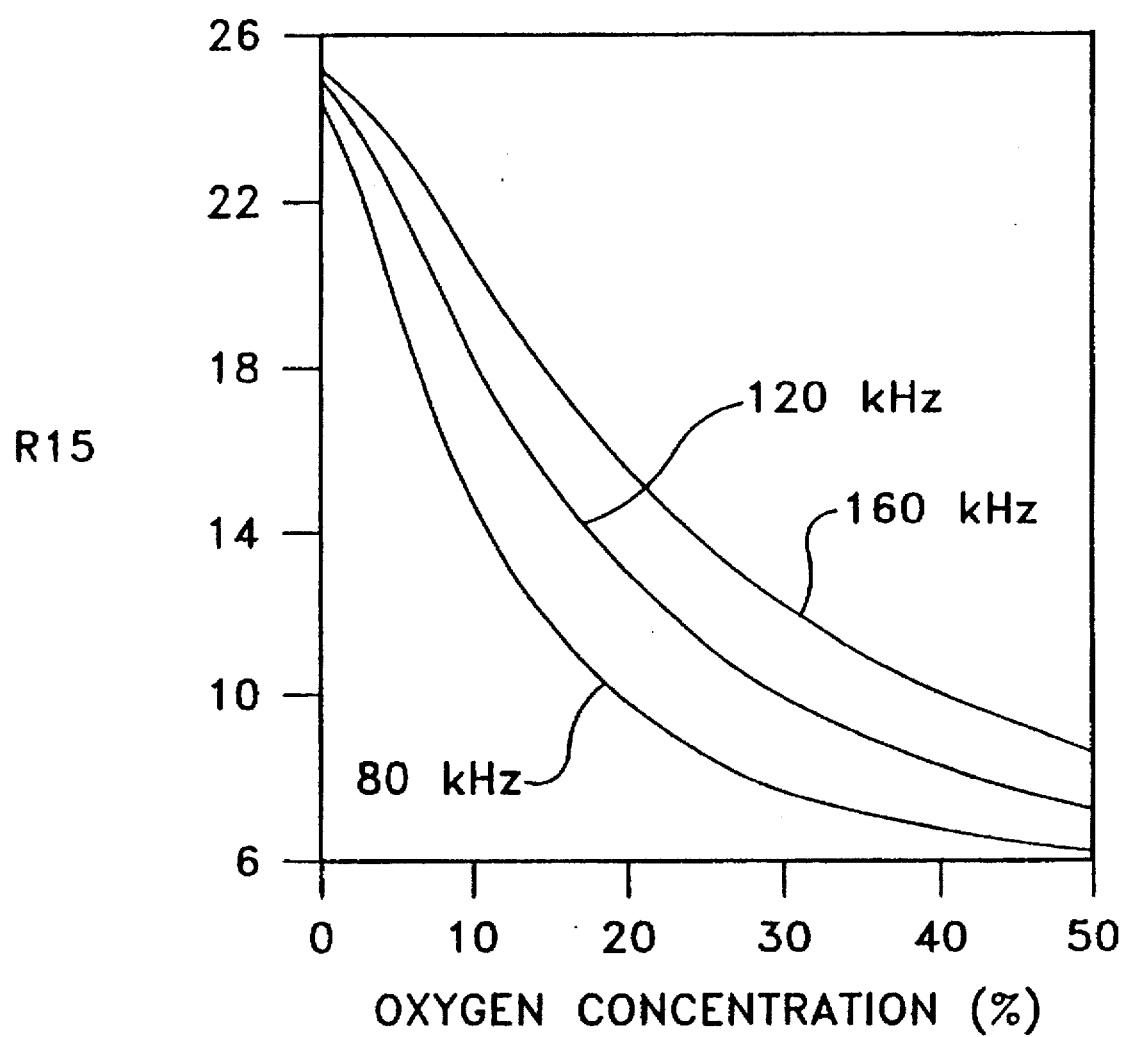
FIG. 5 is plot showing the ratio of the first and the fifth harmonic versus oxygen concentration.

If oxygen consumption is used to detect the presence of microorgansims, then the ratio R51 in FIG. 4 would start at a high level, and would then decrease to a lower level. Therefore, it may be more practical to calculate the ratio R15 which shows an increase over time as consequence of oxygen consumption. FIG. 5 depicts R15 for square-wave frequencies of 80, 120 and 160 kHz, respectively, assuming the same fluorescent sensor as in FIGS. 2 and 4.

Figure 6:
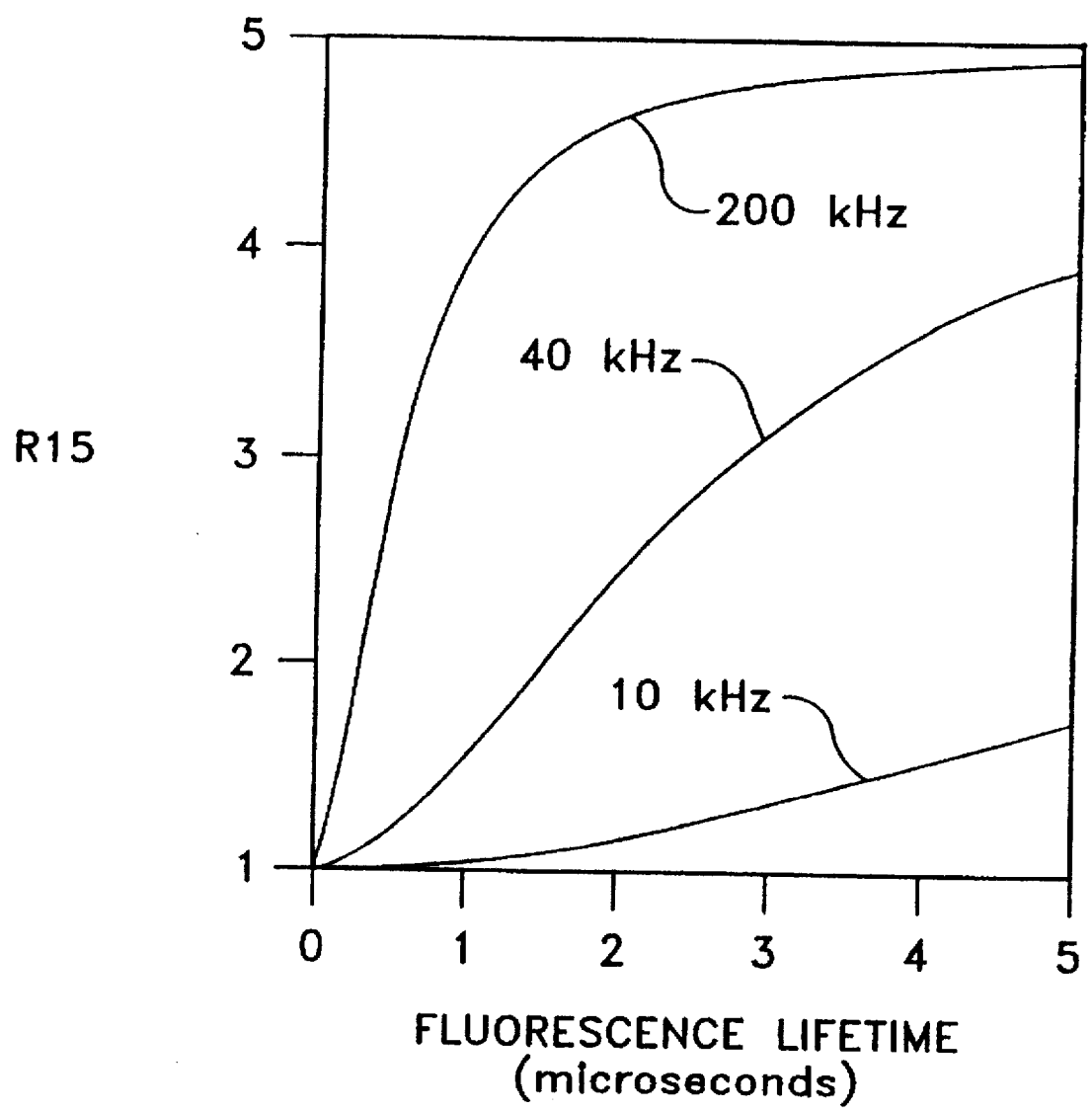
FIG. 6 is a plot showing the ratio of the first and the fifth harmonic versus fluorescence lifetime for a fluorophore that is illuminated with a square-wave modulated light intensity and has a fluorescence lifetime that depends on any sensor input.

It should be appreciated that the scope of the present invention is not limited to fluorophores that are quenched by an analyte according to the Stem-Volmer law shown in Equation (7). FIG. 6 depicts the ratio R15 of the first and the fifth harmonic versus fluorescence lifetime for a fluorophore that is illuminated with a square-wave modulated light intensity and has a fluorescence lifetime that depends on any sensor input. The three curves correspond to square-wave frequencies of 10, 40 and 200 kHz, respectively. However, the same curves would still apply if the fluorescence lifetime was in the. nanosecond range. In that case, the indicated square-wave frequencies would be in the MHz range. As in FIGS. 2 and 4, an almost linear relationship can be established between the sensor output signal and the input. In FIG. 6, we assume that the fluorescence lifetime is linearly dependent on the analyte.

A fluorescence detector according to the present invention has some important advantages over conventional apparatus in the prior art. In measuring two different AC components, instead of measuring an AC component and the DC component, the effect of a change in the dark current of the photodetector, and the effect of daylight leaking into the apparatus are eliminated. Moreover, by selecting an optimum square-wave frequency, the relationship between the sensor output signal and the analyte concentration can be "tailored" to be almost a linear one, so that the sensor resolution becomes independent of the analyte concentration. This linearization can be achieved for sensor materials that follow a typical Stern-Volmer quenching relationship, but also for other sensor materials.

A fluorescence detector according to the present invention is not effected by changes in the excitation light source intensity, small changes in the sample container position, changes in the emission filter characteristics, or changes in the photodetector sensitivity. This is because all these artifacts have the same influence on the two harmonics that are selected and are, therefore, canceled out by ratio unit 12.

It is well-known that lot-to-lot variations in the fluorescence sensor production process can have a major impact on the fluorescence intensity. One major reason are the variations in dye concentration within the sensor material. However, this is not the case with regard to fluorescence lifetime since lifetime is much less sensitive to concentration variations. Consequently, an optical sensor according to the present invention provides an excellent opportunity for high reliability, absolute calibration, and long-time stability. This is especially important if the sensor is used to monitor tuberculosis ("TB") samples that require extraordinary long observation periods covering many days. It would even be possible to arrange a very large number of sample containers on a few portable racks. Removal and subsequent re-entry of these racks into a fluorescence reader in a slightly different position would not cause signal variations.

The scope of the present invention is also not limited to a symmetric square-wave signal. Other asymmetric square-waves with c smaller or larger than π/2, and periodic non-square-wave signals could also be applied. However, a symmetric square-wave signal is a preferred option because it offers the following advantages:

First, a square-wave signal can be generated most easily with high precision, and with a minimum of electronic circuitry.

Secondly, for a symmetric square wave, all even harmonics are equal to zero. This results in a large frequency difference between neighboring harmonics and allows use of band pass filters of low Q values, which are more stable over extended periods of time.

Thirdly, the modulation degree of the excitation light is well-defined and stable over time. Therefore, no source monitor is required to make sure that the excitation light source is still well modulated. This second aspect would have even more importance for a conventional modulation sensor arrangement with AC and DC measurement, where the actual source modulation has a direct impact on the sensor output signal. If a biased sinusoidal signal is utilized to modulate the light source, any drift in the AC/DC ratio will cause an error in the sensor output information. A fluorescence detector according to the present invention, however, is free of such problems.

Fourthly, a symmetric square wave provides a reasonable ratio between the fifth, third and first harmonic, while representing a non-dangerous mode of driving. If one would use shorter pulses, the amplitude ratio between the three harmonics could be better equalized. However, a decreasing c in equation (4) results in lower signal amplitudes for all the harmonics. The decrease in signal amplitude could be compensated by pulsing an LED to much higher forward currents, i.e., by increasing the quantity a in equation (4). By doing so, the danger of damaging the LED increases rapidly and has a negative effect on the life expectancy for the whole detector arrangement.

Finally, the scope of the present invention is not limited to the use of LED's. The invention can also be applied while using diode lasers, internally or externally modulated lasers or other light sources.

A modification of the present invention is given, if a chemical sensor material is illuminated with excitation light which is turned on and off periodically according to a symmetric square wave, and the measured fluorescence photocurrent is analyzed within a computer, which separates digitally the received signal into two AC components that are representing different harmonics of the square-wave signal, calculates the amplitudes of the two components, and generates the ratio of the two components, whereby this ratio is utilized as the sensor output signal.

It should be understood that the above-described embodiment is simply illustrative of an apparatus embodying the principles and concepts of the present invention. Of course, other suitable variations and modifications could also be made to the apparatus and method described and still remain within the scope of the present invention.

What is claimed is:

1. An apparatus for detecting microorganism growth within a container having a culture medium, a blood specimen and a chemically sensitive material, said apparatus comprising;
    an excitation light source for illuminating the chemically sensitive material with a light that is intensity-modulated according to a square wave between the states "ZERO" and "HIGH" to cause the chemically sensitive material to emit a fluorescence in response to a gas being generated or consumed by microorganism growth in a blood specimen;
    means for detecting the fluorescence emerging from the chemically sensitive material;
    means for generating an electrical output signal representative of the fluorescence, e detected by said detecting means;
    a first band pass filter tuned to one harmonic of the intensity-modulated light for filtering the output signal into a first filtered signal, B;
    a second band pass filter tuned to another harmonic of the intensity-modulated light for filtering the output signal into a second filtered signal, A;
    means for calculating an A/B ratio value by dividing of the second filtered signal, A, by the first filtered signal, B; and
    means for generating a sensor output signal representative of detected microorganism growth using the calculated A/B ratio value.

2. An apparatus according to claim 1, wherein said fluorescence light detecting means is a photodetector.

3. An apparatus according to claim 1, further comprising an emission filter arranged between the chemically sensitive material and said fluorescence light detecting means to reject any intensity-modulated light being back-scattered from the container.

4. An apparatus according to claim 1, wherein said harmonic to which said first band pass filter is tuned is a first harmonic of the intensity-modulated light and the harmonic to which said second band pass filter is tuned is a third harmonic of the intensity-modulated light.

5. An apparatus according to claim 1, wherein said harmonic to which said first band pass filter is tuned is a first harmonic of the intensity-modulated light and said harmonic to which said second band pass filter is tuned is a fifth harmonic of the intensity-modulated light.

6. An apparatus according to claim 1, wherein said harmonic to which said first band pass filter is tuned is a third harmonic of the intensity-modulated fight and the harmonic to which said second band pass filter is tuned is a first harmonic of the intensity-modulated light.

7. An apparatus according to claim 1, wherein said harmonic to which said first band pass filter is tuned is a fifth harmonic of the intensity-modulated light and said harmonic to which said second band pass filter is tuned is a rust harmonic of the intensity-modulated light.

8. An apparatus according to claim 1, wherein said square wave is a symmetric square wave with respect to time.

9. An apparatus according to claim 1, wherein said square wave is a non-symmetric square wave with respect to time.

10. An apparatus for detecting microorganism growth within a container having a culture medium, a blood specimen and a chemically sensitive material, said apparatus comprising;
    an excitation light source for illuminating the chemically sensitive material with a light that is periodically intensity-modulated according to a square wave to cause the chemically sensitive material to emit a fluorescence in response to a gas being generated or consumed by microorganism growth in a blood specimen;
    means for detecting the fluorescence emerging from the chemically sensitive material;
    means for generating an electrical output signal representative of the fluorescence detected by said detecting means;
    a first band pass filter tuned to one harmonic of the intensity-modulated light for filtering the output signal into a first filtered signal, B;
    a second band pass filter tuned to another harmonic of the intensity-modulated light for filtering the output signal into a second filtered signal, A;
    means for calculating an A/B ratio value by dividing of the second filtered signal, A, by the first filtered signal, B; and
    means for generating a sensor output signal representative of detected microorganism growth using the calculated A/B ratio value.

* * * * *